United States Patent [19]

Miyazaki et al.

[11] Patent Number: 5,229,302
[45] Date of Patent: Jul. 20, 1993

[54] FLUORESCENCE IMMUNOASSAY METHOD UTILIZING PSEUDO-ANTIGENS COMBINED WITH FLUORESCENT QUENCHERS

[75] Inventors: Jinsei Miyazaki; Noboru Motoyama; Tadayasu Mitsumata, all of Osaka, Japan

[73] Assignee: Matsushita Electric Industrial Co., Ltd., Osaka, Japan

[21] Appl. No.: 830,442

[22] Filed: Feb. 3, 1992

Related U.S. Application Data

[63] Continuation of Ser. No. 330,342, Mar. 28, 1989, abandoned.

[30] Foreign Application Priority Data

Mar. 29, 1988 [JP] Japan .................. 63-75447

[51] Int. Cl.⁵ .......................................... G01N 33/542
[52] U.S. Cl. .................................. 436/537; 436/546; 436/816
[58] Field of Search ............... 436/537, 546, 805, 816

[56] References Cited

U.S. PATENT DOCUMENTS

| | | | |
|---|---|---|---|
| 4,199,559 | 4/1980 | Ullman et al. | 436/537 |
| 4,256,834 | 3/1981 | Zuk et al. | 435/7 |
| 4,261,968 | 4/1981 | Ullman et al. | 424/8 |
| 4,277,437 | 7/1981 | Maggio | 422/61 |
| 4,318,707 | 3/1982 | Litman et al. | 424/8 |
| 4,654,300 | 3/1987 | Zuk et al. | 435/7 |

FOREIGN PATENT DOCUMENTS

1084838 9/1980 Canada .

OTHER PUBLICATIONS

Usagawa et al, "Preparation of Monoclonal Abys Against Methamphetamine", J. Immuno. Methods, 119 (1989) pp. 111–115.
Ullman, E. F., "Fluorescent Excitation Transfer Immunoassay", J. of Biological Chemistry, vol. 251, No. 14 (1976), pp. 4172–4178.
Chemical Abstracts, vol. 109: 207524p (1988), Mitsumata et al, "Apparatus and Method for Enzyme-Linked Immunoassay", p. 207521.
Lakowicz, J. R., "Protein Fluorescence", pp. 2–4.
"Enzyme Immunoassays: Heterogeneous and Homogeneous Systems" by R. M. Nakamura et al; Handbook of Experimental Immunology 4th Edition, vol. 1 and Immunochemistry, Chapter 27; pp. 27.1-27.20.
"Antibody Affinity. VIII. Measurement of Affinity of Anti-Lactose Antibody by Fluorescence Quenching with a DNP-Containing Ligand" by P. V. Gopalakrishnan et al; The Journal of Immunology vol. 114, Apr. 1985; pp. 1359–1362.
Handbook of Experimental Immunology, vol. 1, Blackwell scientific publications, 1979, p. 18.3–18.6 is cited.

Primary Examiner—Mary E. Ceperley
Attorney, Agent, or Firm—Lowe, Price, LeBlanc & Becker

[57] ABSTRACT

A fluorescence immunoassay method is described in which the presence or absence of antigen is measured within one minute by measuring a variation in fluorescence emitted from an antibody. The method comprises reaction between a pseudo-antigen obtained by chemical combination of an antigen and a fluorescent quencher and an antibody by which fluorescence to be emitted from the antibody is quenched by the action of the quencher combined. When an analyte is added to a solution of the combination, the pseudo-antigen is replaced by an antigen if the analyte contains the antigen, so that the fluorescence increases in intensity. This intensity is measured and compared with the initially measured intensity to detect the presence of the antigen. The method does not make use of the action of antigen on antibody with respect to the fluorescence of the antibody and is applicable to all antigens.

14 Claims, 1 Drawing Sheet

FLUORESCENCE IMMUNOASSAY METHOD UTILIZING PSEUDO-ANTIGENS COMBINED WITH FLUORESCENT QUENCHERS

This application is a continuation of application Ser. No. 07/330,342 filed Mar. 28, 1989, now abandoned.

BACKGROUND OF THE INVENTION

1. Field of the Invention

This invention relates to the art of immunological detection and more particularly, a method for the immunological detection wherein there are utilized antibodies capable of binding with analytes or substances to be detected.

2. Description of the Prior Art

Immunological detection utilizing naturally occurring or artificially prepared antibodies has merits in high selectivity and high sensitivity to analytes or objects to be detected and has thus been currently employed for the purpose of detecting analytes present in very small amounts. This detection technique has been applied, for example, to clinical examinations such as of so-called disease markers which are specifically secreted when one suffers diseases accompanied by tumors, cardiac infarction, cerebral thrombosis and the like, or also to detection of substances contained in air in very small amounts. For the detection of these markers or substances, it is usual that the sensitivity for determination of the presence or absence of bound antibody is improved by the use of radioactive isotopes or enzyme reactions. However, the use of radioactive isotope is limited to a laboratory scale test because of the danger involved therein. A number of the detection techniques utilizing the enzyme reactions, i.e. enzyme immunoassays (hereinafter sometimes referred to as EIA), have been proposed using various combinations of the reactions (R. M. Nakamura, A. Voller and D. E. Bidwell, Enzyme Immunoassays: Heterogeneous and Homogeneous Systems in Handbook of Experimental Immunology 4th Edition, Vol. 1 and Immunochemistry, Chapter 27, edited by D. M. Weir, Blackwell Scientific Publications, Oxford, 1986). These EIA methods can be broadly divided into two classes, one being directed to high molecular weight substances or proteins as analyte and the other dealing with low molecular weight analytes, e.g. haptens. Analytes to which the present invention is directed are mainly haptens. Accordingly, an enzyme linked immunosolvent assay (ELISA) which is a typical technique for haptens is illustrated with respect to experimental procedures.

The ELISA technique is generally carried out in the following procedure.

(A) A conjugate of a carrier protein such as, for example, bovine serum alubmin (BSA) analyte or its derivative introduced with a functional group is dissolved in a buffer to form an antigen solution. The antigen solution is added to a microplate (e.g. a polyvinyl chloride or polyethylene 96 well plate) in an amount of 100 μL/well and incubated at 20° C. overnight.

(B) Blocking

A phosphate buffered solution of BSA having a pH of 7.5 is added in an amount of 250 μL/well, followed by allowing to stand at room temperature for 0.5 to 2 hours and washing with a buffer or pure water 3 to 5 times.

(C) Antibody Reaction

A solution of an analyte is added to the well plate, to which an antibody solution is further added while shaking. After keeping it at normal temperatures for 3 to 5 hours, the antibody solution is removed by means of an aspirator, followed by washing with a buffer or pure water three to five times.

(D) Second Antibody Reaction

A solution of an anti-mouse IgG antibody against an antibody labelled with an enzyme such as, for example, peroxidase is added to the washed mixture and allowed to stand at normal temperatures for 0.5 to 2 hours, followed by washing with a buffer or pure water three to five times.

(E) Reaction of Substrate and Its Termination

A color developer such as, for example, o-phenylenediamine is dissolved in a buffer to obtain a solution. Immediately before its application, the solution added with 30% hydrogen peroxide is further added as a substrate solution, followed by color developing reaction at room temperature. Five to twenty minutes after the addition, the reaction is terminated with sulfuric acid.

(F) Measurement

An absorbance at 492 nm is measured by the use of a spectrophotometer for microplate. The absorbance becomes weaker for a larger amount of the analyte, from which the analyte can be quantitatively determined.

As will be apparent from the above, the ELISA technique has the advantage in treating a number of specimens at the same time, but requires the complicated procedure, which in turn requires the skill on the part of a tester. In addition, this technique is difficult to automate, coupled with the further problem that it takes a very long examination time of not shorter than 5 hours. These problems are true of the other EIA techniques set out in the literature indicated above.

The reason why these EIA techniques take a long time and much labor is considered as follows. In most cases, these techniques make use of a procedure of separating antigen-bound antibody and free antibody from each other (B-F separation). This procedure involves either a heterogeneous reaction where solid and liquid phases coexist or a homogeneous reaction in solution where proteins including antibodies react with each other. In either case, the reaction speed is very slow and thus entails an increase of the detection time.

SUMMARY OF THE INVENTION

It is accordingly an object of the invention to provide an immunological method which ensures safe, simple and high speed detection of an antigen to be detected.

It is another object of the invention to provide a fluorescence immunological method which is simple in procedure and is easy to automate.

It is a further object of the invention to provide a fluorescence immunological method whereby an antigen can be detected within a very short time of, for example, not longer than 1 minute since any B-F separation as will be required in prior art procedures is not necessary.

The above objects can be achieved, according to the invention, by a fluorescent immunoassay method which comprises:

providing a solution of a pseudo-antigen which is obtained by chemical combination between a fluorescence quencher having the action or ability of quenching fluorescence emitted from an antibody and an antigen;

adding the solution of the pseudo-antigen to a solution of an antibody capable of emitting fluorescence by irradiation of light, thereby permitting the antigen of the pseudo-antigen and the antibody to be combined; irradiating the solution with the light and measuring an intensity of the fluorescence emitted from the antibody; and adding an analyte to the solution and irradiating the solution with the light to measure a variation in the intensity of the fluorescence, from which the presence of absence of an antigen in the analyte is detected.

DETAILED DESCRIPTION AND EMBODIMENTS OF THE INVENTION

Figure 1:
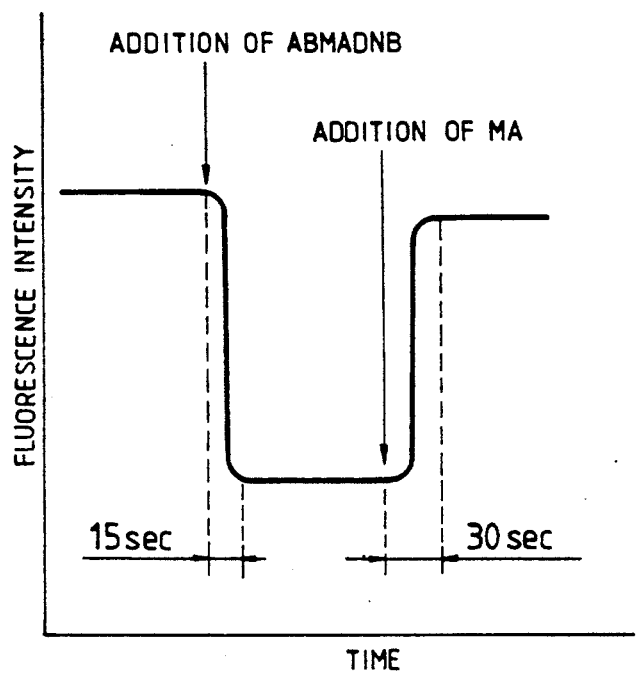
FIG. 1 is a graph showing the relationship between the time and the variation in fluorescence which is determined by the fluorescence quench inhibition immunoassay.

The present invention is based on the principle that a system is provided wherein when an antibody is bound with an antigen, the fluorescence intensity of the antibody is varied, and the presence or absence of the antigen is detected based on the variation of the fluorescence intensity. In this system, the separation between bound antibody and free antibody is not necessary, with a success in remarkable shortage of the detection time.

In the method of the invention, a pseudo-antigen is first provided as a solution in a buffer such as a phosphate buffer, a tris buffer, a citrate buffer and the like. This pseudo-antigen is prepared by chemical linking or binding of an antigen and a fluorescence quencher.

The solution of the pseudo-antigen is added to a solution of antibody whereupon the pseudo-antigen binds with the antibody. In general, when an antibody is excited at approximately 280 nm, fluorescence in the vicinity of 340 nm is emitted therefrom. Accordingly, the irradiation of the solution of the antibody bound with the pseudo-antigen with light having a wavelength of about 280 nm results in emission of the fluorescence. Since the pseudo-antigen has the quencher moiety, the fluorescence emitted from the bound antibody is suppressed to a greater extent than that of the free antibody.

In this state, an analyte is added to the solution. If the analyte contains an antigen this antigen preferentially combines with the antibody by substitution with the pseudo-antigen. Accordingly, once decreased fluorescence increases to an extent corresponding to the content of the antigen in the analyte since the quencher moiety is dissociated. When the increment of the fluorescence determined by the irradiation of the light is measured, the quantitative detection of the antigen becomes possible.

As stated above, when an antibody is irradiated and excited with a UV ray having a wavelength of approximately 280 m, fluorescence is emitted at about 340 nm by the action of amino acids including tryptophane. Although the wavelengths of the excitation light and the emitted light may be increased or decreased by about 30 nm around the above values, respectively. The Raman light of water appearing in the vicinity of the emission light of the antibody becomes a factor of causing noises. In order to minimize the influence of the Raman light, the wavelength used is conveniently about 280 nm for the excitation light and about 340 nm for the emission light.

The pseudo-antigen used in the first step of the method according to the invention is obtained by chemical combination between a fluorescence quencher having the action or ability of quenching fluorescence emitted from an antibody and an antigen.

Studies have been heretofore made on the influences of aromatic nitro compounds such as nitrobenzene, dinitrobenzene and trinitrobenzene on monoclonal antibodies. These aromatic nitro compounds have the capability of quenching fluorescence of antibodies to an extent. This capability has been utilized for measurement of affinity between antibodies and aromatic nitro compounds. Accordingly, if these substances having the capability of quenching fluorescence are an object to be detected, it is possible to directly detect them by measurement of a variation in the intensity of the fluorescence. However, most low molecular weight organic substances such as haptens exhibit no fluorescence quenching capability.

Therefore, we have developed a fluorescence quenching immunoassay which is effective, irrespective of the kind of antigen, by use of pseudo-antigens which are made by chemically linking an antigen and a quencher substance. When bound to antibodies, these compounds are able to lower the fluorescence emitted from antibody upon irradiation of the UV light as discussed above. Although typical compounds which can be a quencher of such pseudo-antigens are aromatic nitro compounds, the present invention should not be limited to these compounds only. All compounds may be used in the practice of the invention so far as they have the fluorescence quenching ability.

For convenience' sake, use of the pseudo-antigen derived from aromatic nitro compounds is described herein.

When the aromatic nitro compounds including nitrobenzene, dinitrobenzene and trinitrobenzene are introduced with functional groups such as a sulfonic acid group, a halogen, an amino group, a carboxyl group, a hydroxyl group, a thiol group, the resultant derivatives allow chemical linking with any antigens. Thus, pseudo-antigens can be conveniently prepared. In practical applications, a possible antigen which is considered to be contained in an analyte may be conveniently used as a counterpart for the aromatic nitro derivatives.

Of the above derivatives of the aromatic nitro compounds, 2,4-dinitrofluorobenzene (DNFB) is preferred because it is readily available as a reagent for determination of the arrangement of amino acid and is readily combined with amino groups irrespective of haptens or proteins. If haptens have no functional groups such as amino groups, the fluorescence quencher may be chemically combined with haptens after introduction of functional groups into the hapten.

The antigens to be combined with an organic low molecular weight compound having the quenching capability may be any antigens including haptens and proteins. Specific examples useful in immunological treatment according to the method of the invention include amphetamine, methamphetamine, ephedrine and the like.

The pseudo-antigens obtained from the organic low molecular weight compounds, particularly aromatic nitro derivatives, and antigens have the function as an antigen which is to be bound with an antibody and the function to quench fluorescence of the antibody. The pseudo-antigen is applied in a subsequent step in the form of a solution in a buffer as set out before.

Specific and, in fact, preferable pseudo-antigens are derived from methamphetamine or its derivative and 2,4-dinitrofluorobenzene and represented by the following formula

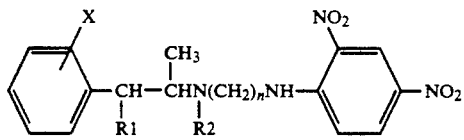

wherein X represents hydrogen or —$OCH_3$, R1 represents hydrogen or —OH, R2 represents hydrogen or —$CH_3$, and n is 0 or a positive number. The preparation of this pseudo-antigen is particularly described in examples appearing hereinafter. More specific examples of the pseudo-antigen are shown below.

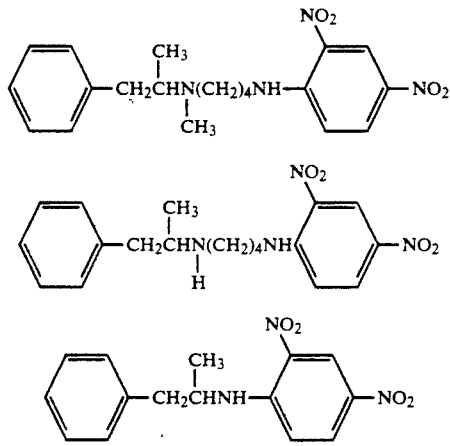

Next, the pseudo-antigen is added to a solution of an antibody capable of emitting fluorescence by irradiation of light having a wavelength which is discussed before. By the addition, the pseudo-antigen binds to the antibody. In order to effectively cause a fluorescence quenching inhibition reaction in a subsequent step, the solution should preferably have a concentration of the antibody as small as possible provided that a variation of fluorescence is detectable. The concentration may differ depending upon the type of antibody and is generally in the range of $10^{-6}$ to $10^{-9}$M. The reaction is completed, for example, within about 30 seconds.

After the binding, the light having such a wavelength as defined above is irradiated to measure an intensity of the fluorescence emitted from the antibody. When compared with an intensity of the fluorescence from the antibody solution, it decreases corresponding to a degree of the binding of the pseudo-antigen and the antibody owing to the action of the fluorescence quencher.

In case where amphetamine, methamphetamine or ephedrine is used as an antigen for the pseudo-antigen, the antibody used in this step should preferably be a monoclonal antibody capable of binding with amphetamine, methamphetamine or ephedrine.

Finally, an analyte or a substance to be detected is added to the solution in amounts not impeding its optical detection. If an antigen is contained in the analyte, this antigen preferentially combines with the antibody by substitution with the combined pseudo-antigen. In other words, the antigen contained in the analyte causes the pseudo-antigen and the antibody to dissociate and reacts with the dissociated antibody. As a result, the fluorescence emitted from the substituted antibody increases when irradiated with the light having a wavelength of about 280 nm. This is because the quencher is removed from the antibody so that the antibody can emit fluorescence at a higher intensity. The measurement of the intensity of fluorescence can reveal the presence or absence of the antigen in the analyte by comparison with the intensity of the fluorescence after the combination between the pseudo-antigen and the antibody.

This fluorescence quenching inhibition immunoassay according to the invention does not make use of a fluorescence variation characteristic of antigen relative to antibody and ensures a high speed fluorescence immunological measurement of all antigens.

When aromatic nitro derivatives are used, the degree of the fluorescence quenching generally reaches about 20% or over, leading to high sensitivity of the detection. Accordingly, for the preparation of monoclonal antibodies, choice of cell lines for the purpose of directing attention to fluorescence quenching properties is not necessary. This makes it possible to prepare such antibodies with a view to enhancing affinity for the pseudo-antigen.

The present invention is described in more detail by way of examples.

EXAMPLE 1

Synthesis of a pseudo-antigen is briefly described.

According to a known procedure (Tamaki, Fukuda and Takahashi, Jpn, J., Legal Med., 37(4), 417, 1983), N-(4-aminobutyl)methamphetamine of the following structural formula (hereinafter abbreviated as ABMA) was prepared.

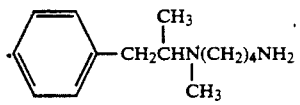

The ABMA and 2,4-dinitrofluorobenzene were mixed in equimolar amounts in acetone and agitated for 1 hour, followed by purification by the use of a thin layer chromatography for collection. As a result, a pseudo-antigen, N-(2,4-dinitrophenyl)-N'-(4'-aminobutyl)methamphetamine (DNPABMA), having the following structural formula was obtained.

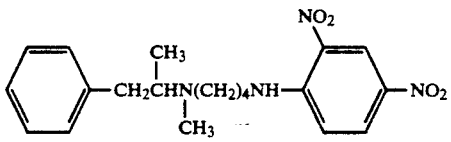

The antibody used in this example was anti-methamphetamine monoclonal antibody (hereinafter abbreviated as MAB1) prepared by us in the following manner.

1) Mice were each immunized with conjugate of N-(4-aminobutyl)amphetamine and key hole limplet hemocyanine (ABAPKLH).

2) Four months after the immunization, spleen cells were extracted from the mice and fused with myeloma cells from another mouse to make hybridoma cells.

3) Hybridoma cells which were able to produce antibody in high affinity for MA were selected and cloned by a known procedure.

4) The selected hydridoma were cultured, and monoclonal antibody was isolated from the culture through protein-A affinity chromatography column.

This antibody was developed to impart affinity for methamphetamine (MA) and had an affinity of about $10^8$ but did not exhibit little fluorescence reinforcing action. In other words, the antibody was nothing other than those prepared by the most common procedure.

The fluorescence quenching inhibition immunoassay according to the invention using the antibody is described.

(A) MAB1 was dissolved in a buffer obtained by passing a phosphate buffer having a pH of 7 through a $0.45\mu$ filter to make a concentration of $1.9 \times 10^{-7}$M. 360 $\mu$L of this solution were placed in a microcell for fluorescence measurement. The solution was excited with excitation light having a wavelength of 280 nm (bandpass 5 nm), whereupon fluorescence having a wavelength of 340 nm (bandpass 10 nm) was emitted with an intensity of about 61.5 (FL0).

(B) 20 $\mu$L of each of buffer solutions of DNPABMA having different concentrations was added to the solution in (A). As a result, quenching took place with a reduction of the fluorescence intensity (FL1). As the concentration of DNPABMA increased, the value of FL1/FL0 decreased. At the concentration of DNPABMA of $10^{-5.5}$ (final concentration), the value of FL1/FL0 reached a saturation of 60%.

In order to more efficiently conduct the fluorescence quenching inhibition reaction in a subsequent step, the concentration of a pseudo-antigen, e.g. DNPABMA, is preferably as low as possible within a range where the variation in fluorescence can be detected.

In this example, the concentration of DNPABMA used was $10^{-11}$M (final concentration). The quenching reaction reached an equilibrium in about 15 seconds.

(C) 20 $\mu$L of each of MA buffer solutions having different concentrations was added to the solution in (B), whereupon the antibody and MA bound together while dissociating the pseudo-antigen, DNPABMA, thereby impeding the quenching. As a result, the fluorescence intensity increased as FLx. This quenching inhibition reaction reached an equilibrium in about 30 seconds.

The variation of the fluorescence intensity in the above procedure is schematically shown in FIG. 1.

Figure 2:
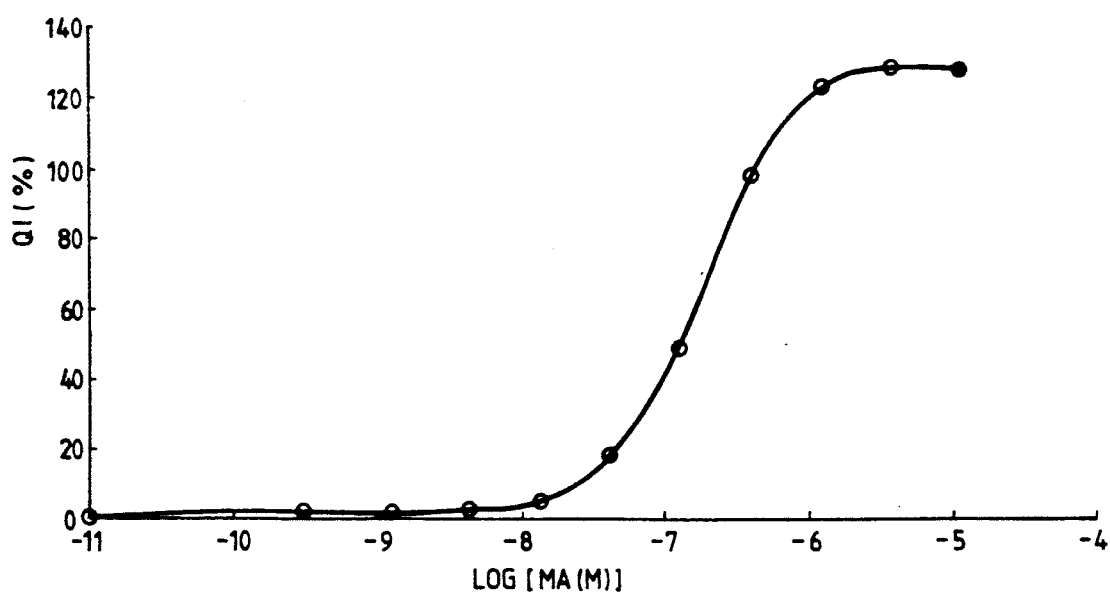
FIG. 2 is a graph showing the relationship between the concentration of methamphetamine used as an antigen and the rate of fluorescence quench inhibition which is determined by the immunoassay as used in FIG. 1.

As will become apparent from the above, when MA is added to the solution of (B), the fluorescence intensity increases, from which the presence of the MA is detectable. In order to confirm the detection sensitivity under the above test conditions, a variation in the fluorescence intensity which was determined using different concentrations of MA is shown in FIG. 2. In FIG. 2, the concentration of MA is a final concentration. The quenching inhibition (QI, %) in the ordinate of FIG. 2 is defined as follows:

$$QI\ (\%) = \frac{FLx - FL1}{FL0 - FlI} \times 100$$

As will be seen from FIG. 2, MA having a concentration of about $10^{-7.5}$M was detected by the fluorescence quenching inhibition immunoassay.

EXAMPLE 2

The general procedure of Example 1 was repeated except that there was used instead of DNPABMA a compound of the following structural formula as a pseudo-antigen. As a result, similar results were obtained but the sensitivity was down to $10^{-6.5}$M.

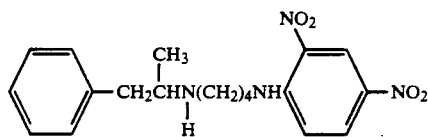

EXAMPLE 3

The general procedure of Example 1 was repeated except that there was used instead of DNPABMA a compound of the following structural formula as a pseudo-antigen. As a result, similar results were obtained but the sensitivity was down to $10^{-6.5}$M as in Example 2.

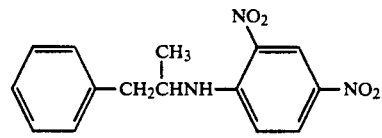

In the foregoing examples, the method of the invention is illustrated for detection of MA, but may be applicable to detection of any other substances. In addition, the dinitrobenzene derivatives were used in the examples since they are readily available, but similar effects can be obtained using other quenchers including nitrobenzene and trinitrobenzene derivatives.

What is claimed is:

1. A fluorescence immunoassay method for determining the presence of an antigen in a sample, which comprises providing a solution of a pseudo-antigen comprising a fluorescence quencher and an antigen which are chemically bound to one another;

adding the pseudo-antigen to a solution of a fluorescent antibody having affinity for the antigen and allowing the antibody to bind the pseudo-antigen;

irradiating the solution with light and measuring the intensity of the fluorescence emitted by the antibody;

adding to the solution a sample comprising an amount of an analyte, irradiating the solution with similar light and measuring the intensity of quenched antibody fluorescence; and determining the presence of the analyte in the sample from any increase in fluorescence intensity; wherein the quencher is a compound selected from the group consisting of a nitrobenzene derivative, a dinitrobenzene derivative and a trinitrobenzene derivative, said derivative having at least one group capable of binding chemically to the antigen.

2. The fluorescence immunoassay method of claim 1, wherein the quencher is a dinitrobenzene derivative.

3. The fluorescence immunoassay method of claim 1, wherein the antibody is a monoclonal antibody capable of binding specifically to an antigen or analyte containing a molecule selected from the group consisting of amphetamine, methamphetamine and ephedrine.

4. The fluorescence immunoassay method of claim 1, wherein
the antigen comprises a molecule selected from the group consisting of amphetamine, methamphetamine and ephedrine.

5. The fluorescence immunoassay method of claim 1, wherein
the pseudo-antigen is a compound of the formula

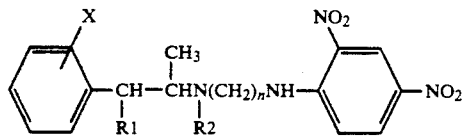

wherein
x represents hydrogen or $OCH_3$,
R1 represents hydrogen or OH;
R2 represents hydrogen or $CH_3$; and
n is 0 or number from 1–4 and
the analyte is amphetamine, methamphetamine or ephedrine.

6. The fluorescence immunoassay method of claim 5, wherein
the pseudo-antigen has the formula

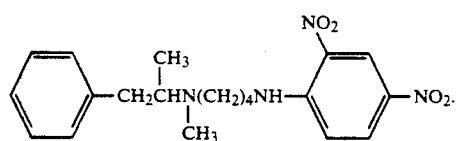

7. The fluorescence immunoassay method of claim 5, wherein
the pseudo-antigen has the formula

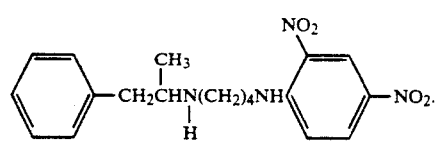

8. The fluorescence immunoassay method of claim 5, wherein
the pseudo-antigen has the formula

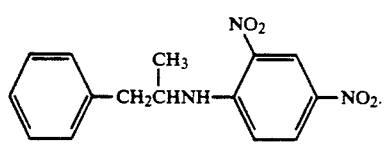

9. The fluorescence immunoassay method of claim 1, wherein
the irradiating light comprises light of a wavelength of about 280 nm.

10. The fluorescence immunoassay method of claim 5, wherein
the concentration of pseudo-antigen in the solution is within a range which permits the fluorescence intensities to be measured with and without the analyte being detected and the analyte is amphetamine, methamphetamine and ephedrine.

11. A fluorescence immunoassay method, which comprises
providing a solution of a pseudo-antigen comprising a methamphetamine derivative of the formula

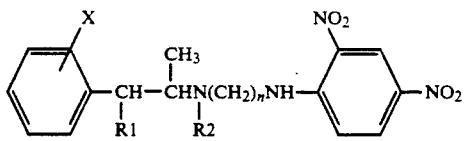

wherein X represents hydrogen or $OCH_3$, R1 represents hydrogen or OH, R2 represents hydrogen or $CH_3$, and n is 0 or a number from 1–4, and a fluorescence quencher selected from the group consisting of a nitrobenzene derivative, a dinitrobenzene derivative and a trinitrobenzene derivative, said derivative having a group capable of binding chemically to the methamphetamine; the methamphetamine and the quencher being bound to one another;

adding the solution of the pseudo-antigen to a solution of an antibody having affinity for the methamphetamine which fluoresces when irradiated with light of about 280 nm wavelength, and allowing the methamphetamine to bind the antibody;

irradiating the solution with light of about 280 nm wavelength and measuring the intensity of fluorescence emitted at 340 nm by the quenched antibody;

adding an analyte sample suspected of comprising an analyte selected from the group consisting of amphetamine, methamphetamine or ephedrine to the solution, irradiating the solution with light at about 280 nm wavelength and measuring the intensity of antibody fluorescence at about 340 nm; and determining the presence of any specific analyte in the analyte sample by comparing the measured intensities.

12. The fluorescence immunoassay method of claim 11, wherein
the pseudo-antigen has the formula

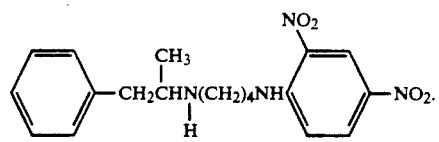

13. The fluorescence immunoassay method of claim 11, wherein
the pseudo-antigen has the formula

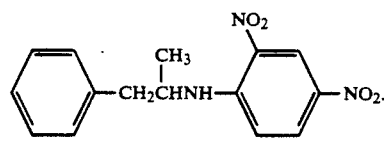

14. The fluorescence immunoassay method of claim 11, wherein
the quencher comprises a dinitrobenzene derivative.

* * * * *